(12) United States Patent
Curtze et al.

(10) Patent No.: US 6,242,498 B1
(45) Date of Patent: Jun. 5, 2001

(54) FUNGICIDAL 2,6,6'-TRIMETHYLBENZOPHENONES

(76) Inventors: Juergen Curtze, Rheingaublick 6, D-65366 Geisenheim; Werner Simon, In derLiehwiese 29, D-55595 Hueffelsheim; Andreas Waldeck, Uferstrasse 17, D-55262 Heidesheim; Henry Van Tuyl Cotter, Eisenacherstrasse 49; Annerose Rehnig, Rathenaustrasse 11, both of D-55218 Ingelheim, all of (DE)

( * ) Notice: Subject to any disclaimer, the term of this patent is extended or adjusted under 35 U.S.C. 154(b) by 0 days.

(21) Appl. No.: 09/129,354

(22) Filed: Aug. 5, 1998

Related U.S. Application Data

(60) Provisional application No. 60/056,573, filed on Aug. 20, 1997.

(51) Int. Cl.[7] .......................... C07C 49/84; A01N 31/16; A01N 35/04
(52) U.S. Cl. .......................... 514/687; 514/687; 568/333
(58) Field of Search .............................. 568/333; 514/687

(56) References Cited

U.S. PATENT DOCUMENTS 5,679,866 * 10/1997 Curtze et al. ........................ 568/333
5,922,905 * 7/1999 Cutze et al. ........................ 562/475

FOREIGN PATENT DOCUMENTS 0 727 141   8/1996 (EP) .............................. A01N/35/04

OTHER PUBLICATIONS

Shein et al. (abstract of Zh. Org. Khim. 4(12), 2160–5 (1968).*

* cited by examiner

Primary Examiner—Sabiha N. Qazi

(57) ABSTRACT

Substituted benzophenone compounds and a process for manufacturing them, are disclosed. The compounds have the formula:

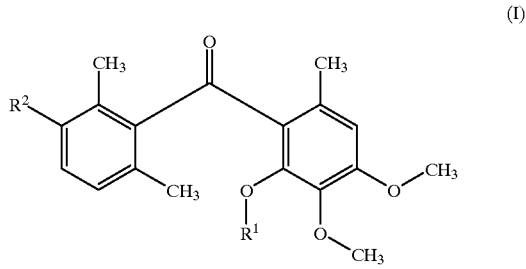

(I)

The compounds are useful as fungicides having high systemicities.

17 Claims, No Drawings

FUNGICIDAL 2,6,6'-TRIMETHYLBENZOPHENONES

This application claims priority of provisional application No. 60/056,573 filed on Aug. 20, 1997.

BACKGROUND OF THE INVENTION

This invention relates to certain 2,6,6'-trimethylbenzophenone compounds, a novel process for their preparation, compositions containing such compounds, a method for combating a fungus at a locus comprising treating the locus with such compounds and their use as fungicides.

Food production relies upon a variety of agricultural technologies to ensure the growing population's dietary needs remain affordable, nutritious and readily available on grocery store shelves. Fungicides are one of these agricultural technologies which are available to the world community. Fungicides are agrochemical compounds which protect crops and foods from fungus and fungal diseases. Crops and food are constantly threatened by a variety of fungal organisms, which, if left uncontrolled, can cause ruined crops and devastated harvests.

In particular, ascomycetes, the causative agent for powdery mildew diseases are an ever-present threat especially to cereal and fruit crops. However, applications of fungicidal agents at disease control rates can cause phytotoxic damage to the target plants.

The compounds of the present invention are disclosed in a broad general formula of the European patent ("EP") application EP 0 727 141, which published on Aug. 21, 1996. The EP application discloses compounds having activity against phytopathogenic fungi, but relatively low systemicity.

There is no disclosure in the EP application of substituted benzophenones, wherein the first phenyl group is substituted by two methyl groups in the 2- and 6-position and an additional substituent in the 3-position.

Moreover, there is no hint given to a one-step process in which a methoxy group in the 2-position of the second phenyl group is directly replaced by an alkoxy group.

SUMMARY OF THE INVENTION

The present invention provides a process for the preparation of a compound of formula I,

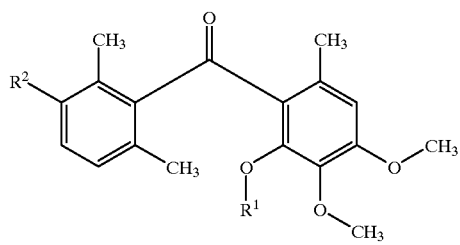
(I)

in which
R$^1$ represents an optionally substituted C$_2$–C$_6$ alkyl, benzyl, cyclohexylmethyl or C$_3$–C$_6$ alkenyl group, and
R$^2$ represents a hydrogen or a halogen atom, or an optionally substituted alkoxy group or a nitro group, which comprises reacting a compound of formula II,

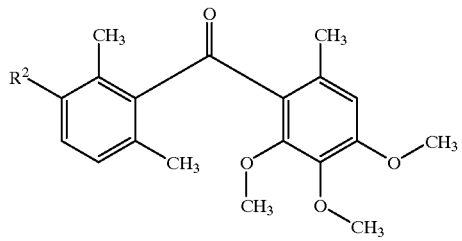
(II)

wherein R$^2$ has the meaning given, with a compound of formula III,

R$^1$—O—Met (III)

wherein R$^1$ has the meaning given and Met denotes an alkali metal atom.

Moreover, the present invention relates to novel compounds of compound of formula IA:

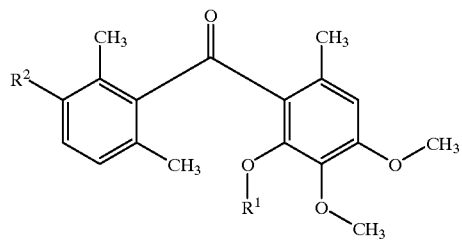
(IA)

wherein R$^1$ has the meaning given above, and R$^2$ represents a halogen atom, or an optionally substituted alkoxy group or a nitro group.

Furthermore, the present invention relates to novel compounds of formula IIA:

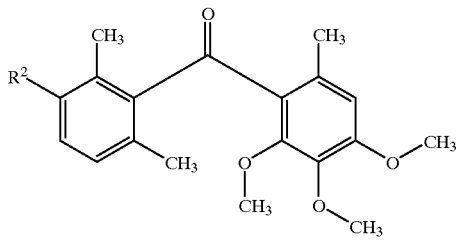
(IIA)

wherein R$^2$ represents a halogen atom, or an optionally substituted alkoxy group or a nitro group.

The compounds combine relatively excellent selective fungicidal activities in various crops with comparably high systemicities.

It is an object of the present invention to provide highly systemic fungicidal compounds.

It is also an object of the invention to provide methods for controlling an undesired fungus by contacting said plants with a fungicidally effective amount of the compounds.

It is another object of the invention to provide selective fungicidal compositions containing the compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of formula I

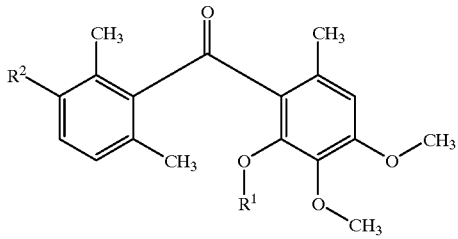

(I)

can easily be prepared from compounds of formula II

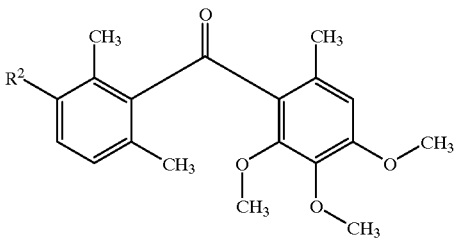

(II)

by reaction with a compound of formula III $R^1$—O—Met     (III)

in which $R^1$, $R^2$, and Met have the meaning given above, in high yields. The $R^1$—O group selectively substitutes the methoxy group attached in the 2-position with respect to the benzoyl group without affecting the methoxy groups attached in the 3- and 4-position of the right-hand phenyl group. The compounds of formulae IA and IIA, which correspond to formulae I or II, but in which the radical $R^2$ is different from hydrogen, combine relatively excellent fungicidal activity against phytopathogenic fungi even at low dose rates, in particular those that cause powdery mildew diseases and have comparably high systemicity.

In general terms, unless otherwise stated, as used herein the term halogen atom may denote a bromine, iodine, chlorine or fluorine atom, and is especially a bromine, chlorine or fluorine atom.

Optionally substituted moieties may be unsubstituted or have from one up to the maximal possible number of substituents. Typically, 0 to 2 substituents are present. Each optionally substituted group independently is substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, mono- di- or trihalo-phenyl or pyridyl groups.

In general terms, unless otherwise stated herein, the terms alkyl, alkenyl and alkoxy as used herein with respect to a radical or moiety refer to a straight or branched chain radical or moiety. As a rule, such radicals have up to 10, in particular up to 6 carbon atoms. Suitably an alkyl or alkoxy moiety has from 1 to 6 carbon atoms, preferably from 1 to 5 carbon atoms. A preferred alkyl moiety is the methyl, ethyl, n-propyl, isopropyl or n-butyl group.

The invention especially relates to compounds of the general formulae IA and IIA in which any alkyl part of the groups $R^1$ and $R^2$, which may be straight chained or branched, contains 1 to 10 carbon atoms, preferably 1 to 9 carbon atoms, more preferably 1 to 6 carbon atoms, and in which each optionally substituted group independently is substituted by one or more halogen atoms or nitro, cyano, cycloalkyl, preferably $C_{3-6}$ cycloalkyl, cycloalkenyl, preferably $C_{3-6}$ cycloalkenyl, haloalkyl, preferably $C_{1-6}$ haloalkyl, halocycloalkyl, preferably $C_{3-6}$ halocycloalkyl, alkoxy, preferably $C_{1-6}$ alkoxy, haloalkoxy, preferably $C_{1-6}$ haloalkoxy, phenyl, or pyridyl groups, in which the phenyl moiety is optionally substituted by one to three substituents selected from halogen atoms, cyano, $C_{1-6}$ alkyl and $C_{1-6}$ alkoxy groups.

The invention especially relates to compounds of the general formula IA in which $R^1$ represents a straight-chained or branched $C_{2-10}$ alkyl, in particular a straight-chained $C_{2-6}$ alkyl group, most preferably being anethyl, n-propyl, n-butyl, n-pentyl group or a phenylmethyl group, in which the phenyl moiety may be unsubstituted or substituted by 1 to 5, preferably 1 to 3, substituents selected from the group consisting of halogen atoms, alkyl, alkoxy, haloalkyl and haloalkoxy groups.

The invention especially relates to compounds of the general formulae IA and IIA in which $R^2$ represents a halogen atom, in particular a fluorine, chlorine, bromine or iodine atom, a nitro, a $C_{1-10}$ alkoxy or a $C_{1-10}$ haloalkoxy group, most preferred being a chlorine or bromine atom or a nitro or methoxy group.

The benzophenone compounds according to formulae IA and IIA are oils, gums, or, predominantly, crystalline solid materials and possess valuable fungicidal properties. For example, they can be used in agriculture, or related fields such as horticulture and viticulture, for the control of phytopathogenic fungi, especially ascomycetes, in particular powdery mildew diseases such as those caused by *Erysiphe graminis, Podosphaera leucotricha, Uncinula necator* and the like. Said benzophenone compounds possess a high fungicidal activity over a wide concentration range and may be used in agriculture without harmful phytotoxic effects.

Moreover, the compounds according to the invention show enhanced curative and residual control of fungi and fungal diseases such as cereal, cucumber and grape powdery mildew, and improved foliar systemicity compared with conventional fungicides.

Useful results in terms of control of phythopathogenic fungi are obtained with a compound as defined in formula IA and IIA, wherein $R^2$ represents a chloro or bromo atom or a methoxy or nitro group; $R^1$ in formula IA represents preferably an ethyl, n-propyl, butyl, n-pentyl group, or a benzyl group being optionally substituted by halogen;

In particular the compounds of formula A are preferred:

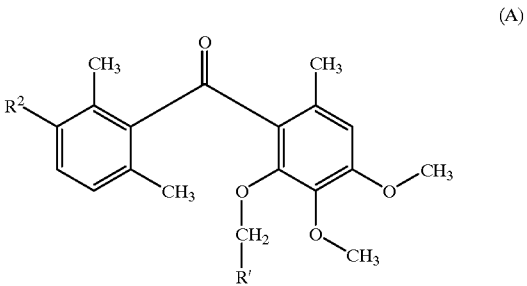

(A)

in which

R² represents a chloro or bromo atom or a methoxy or nitro group, and R' represents a hydrogen atom or a C$_{1-5}$ alkyl or a phenyl group being optionally substituted by one or more fluorine or chlorine atoms or one or more C$_{1-4}$ alkyl groups.

Especially good results in terms of control of phytopathogenic fungi are obtained by using, for example, the following compounds of formula A:

3-bromo-2'-butyloxy-3',4'-dimethoxy-2,6,6'-trimethylbenzophenone,
2'-butyloxy-3-chloro-3',4'-dimethoxy-2,6,6'-trimethylbenzophenone,
2'-butyloxy-3',4'-dimethoxy-3-nitro-2,6,6'-trimethylbenzophenone,
2'-butyloxy-3,3',4'-trimethoxy-2,6,6'-trimethylbenzophenone,
3-bromo-2'-benzyloxy-3',4'-dimethoxy-2,6,6'-trimethylbenzophenone,
3-bromo-3,4'-dimethoxy-2'-(2-fluorobenzyloxy)-2,6,6'-trimethylbenzophenone,
3-chloro-3',4'-dimethoxy-2'-(2-fluorobenzyloxy)-2,6,6'-trimethylbenzophenone,
3',4'-dimethoxy-2'-(2-fluorobenzyloxy)-3-nitro-2,6,6-trimethylbenzophenone,
2'-(2-fluorobenzyloxy)-3,3',4'-trimethoxy-2,6,6'-trimethylbenzophenone,
3-bromo-2',3',4'-trimethoxy-2,6,6'-trimethylbenzophenone,
3-chloro-2',3',4'-trimethoxy-2,6,6'-trimethylbenzophenone,
3-nitro-2',3',4'-trimethoxy-2,6,6'-trimethylbenzophenone,
2',3,3',4'-tetramethoxy-2,6,6'-trimethylbenzophenone.

The present invention further provides a process for the preparation of a compound of formula I, which comprises treating a compound of the general formula II:

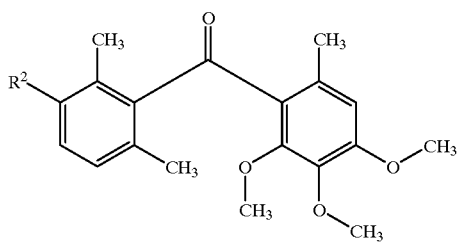

(II)

wherein R² has the meaning given, with a compound of formula III,

R¹—O—Met          (III)

wherein R¹ has the meaning given and Met denotes an alkali metal atom.

The starting materials of formula II, wherein R² represents a hydrogen atom (e.g. EP 0 727 141), and III are known products, and may themselves be prepared according to established methods or routine adaptations thereof. Substituents which are not compatible with the selected reaction conditions may be introduced after formation of the benzophenone. They may be generated by known methods such as subsequent derivatization or substitution of a suitable group or by cleaving off a suitable protecting group.

The novel compounds of formula IIA preferably are prepared by a process which comprises (a) reacting a compound of formula IV,

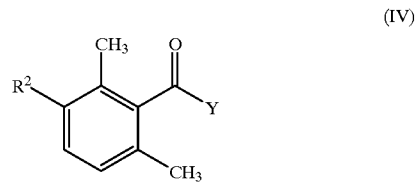

(IV)

wherein R² has the meaning given above and Y represents a leaving group, in particular a chloro atom or a hydroxy group, with 3,4,5-trimethoxytoluene in the presence of a Lewis acid (Y=leaving group) or a dehydrating agent (Y=OH), preferably phosphorous pentoxide or POCl₃.

The reaction between the compounds of formula II and the compound of formula III is preferably carried out in the presence of a solvent, such as ethers like tetrahydrofuran, diethylether, tert-butylmethylether or dimethoxyethane or an alcohol of formula R¹—OH or in mixtures of these solvents. The molar ratio between formula II and III is preferably in the range of 0.3 to 1.9 at a temperature between 25 and 150 °C.

As a rule an alcohol of formula R¹—OH is treated with a strong base, preferably an alkali metal such as sodium, an alkali metal hydride such as sodium hydride, an alkyllithium compound such as n-butyllithium or an alkali metal amide such as sodium amide. In a preferred embodiment the alcohol is treated with sodium hydride until the formation of hydrogen ceases. Subsequently, the compound of formula II or a mixture of the compound of formula II and an inert solvent, in particular dimethoxyethane, is added and the resulting reaction mixture heated to a temperature between 50 and 120° C., in particular between 70 and 100 °C.

The compounds of formula II are preferably prepared by a Friedel Crafts reaction between the compound of formula IV and 3,4,5-trimethoxytoluene. The Friedel Crafts reaction is effected in the presence of a Lewis acid catalyst according to well-established procedures (Y=Cl). Suitable catalysts include FeCl₃, AlCl₃, SnCl₄, ZnCl₂, TiCl₄, SbCl₅ and BF₃, which may be in a molar equivalent amount (based on the benzoyl chloride of formula IV). However, it is also possible to use lesser amounts of catalyst at elevated temperatures, suitably under reflux temperatures, preferred catalysts under these conditions being FeCl₃, I₂, ZnCl₂, iron, copper, strong sulphonic acids such as F₃CSO₃H, and acidic ion exchange resins such as Amberlyst® 15 and Nafion®. The preferred catalyst is FeCl₃ in a 0.001 to 0.2 molar ratio at a temperature of about 50 to 180° C. The reaction can be carried out in a solvent inert under the reaction conditions, for example ethylene or methylene chloride, benzene, octane, decane or solvent mixtures, or in the absence of solvent, conveniently by employing one of the reactants in excess, e.g. in the range of 1:5 to 5:1. If AlCl₃ is being used, the molar ratio is preferably in the range of 0.5 to 2 and the suitable solvents are e.g. methylenechloride or ethylenechloride at a temperature usually between −10 and 70° C.

The compounds of formula IV, wherein R² represents a halogen atom, are preferably prepared by a process which comprises the steps of:

(a) reacting 2,6-dimethylbenzonitril with a halogenating agent in the presence of a Lewis acid, such as aluminium chloride; and (b) hydrolysing the resulting 3-halo-2,6-dimethylbenzonitril with a strong acid, such as sulfuric acid.

The compounds of formula IV, wherein $R^2$ represents a nitro group, are preferbly prepared by treating 2,6-dimethylbenzoic acid with a mixture of sulfuric acid and nitric acid.

The compounds of formula IV, wherein $R^2$ represents an alkoxy group, are preferably prepared by by a process which comprises the steps of:

(a) reducing a compound of formula IV, wherein $R^2$ represents a nitro group;

(b) treating the resulting 3-amino-2,6-dimethylbenzoic acid with aqueous sodium nitrite;

(c) reacting the resulting 3-hydroxy-2,6-dimethylbenzoic acid with an alkylating agent of formula R"—Y", in which R" represents an alkyl group and Y" represents a leaving group, in particular a halogen atom or a group of formula —O—SO$_2$—OR", in which R" has the meaning given.

The processes described below can analogously be applied to other starting compounds, if desired.

Due to excellent plant tolerance, the compounds of formulae IA and IIA may be used in cultivation of all plants where infection by the controlled fungi is not desired, e.g. cereals, vegetables, legumes, apples, vine. The absence of target crop phytotoxicity at fungus control rates is a feature of the present invention.

Accordingly the invention further provides a fungicidal composition which comprises a carrier and, as active ingredient, at least one compound of formula IA or IIA as defined above. A method of making such a composition is also provided which comprises bringing a compound of formula IA or IIA as defined above into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including material which is normally gaseous but which has been compressed to form a liquid, and any of the carriers normally used in formulating fungicidal compositions may be used.

The compositions may be manufactured into e.g. emulsion concentrates, solutions which may be sprayed directly or diluted, diluted emulsions, wettable powders, soluble powders, dusts, granulates, waterdispersible granulates, microencapsulates by well-established procedures. The form of application such as spraying, atomizing, dispersing, pouring may be chosen like the compositions according to the desired objectives and the given circumstances.

The formulations, i.e. the compositions which comprise at least one compound according to general formula I and optionally solid and/or liquid auxiliaries and adjuvants, may be prepared by well-established procedures, e.g. intensive mixing and/or grinding of the active ingredients with other substances, such as fillers, solvents, solid carriers, and optionally surfaceactive compounds or adjuvants.

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, dimethyl sulphoxide, alkyl formamides, epoxidized vegetable oils, e.g. epoxidized coconut or soybean oil, water. Mixtures of different liquids are often suitable.

Solid carriers, which may be used for dusts or dispergible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Fungicidal compositions are often formulated and transported in concentrated form which is subsequently diluted by the user before application. The presence of small amounts of a carrier which is a surface-active agent facilitates this process of dilution. Thus, preferably one carrier in a composition according to the invention is a surface active agent. For example, the composition may contain at least two carriers, at least one of which is a surface active agent.

Suitable surface-active substances may be non-ionogenic, anionic or cationic surfactants with good dispersing, emulgating and wetting properties depending on the nature of the compound according to general formula I to be formulated. Surfactants may also mean mixtures of surfactants.

Suitable surfactants may be so-called water-soluble soaps as well as water-soluble synthetic surface-active compounds.

Soaps usually are alkali, earth alkali or optionally-substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyltaurine salts of fatty acids may be used.

However, so-called synthetic surfactants are preferably used, especially fatty sulphonates, fatty sulphates, sulphonated benzimidazole derivatives or alkyl aryl sulphonates.

The fatty sulphates or fatty sulphonates are normally used as alkali, earth alkali or optionally-substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde.

Furthermore, phosphates, such as the salts of the phosphoric acid ester of a p-nonylphenol-(4-14)-ethylene oxide adduct or phospholipids, may be used.

Non-ionic surfactants are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols.

Other suitable non-ionic surfactants are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit.

Examples of non-ionic surfactants are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol.

Furthermore, fatty acid esters of polyoxy ethylene sorbitan, such as polyoxy ethylene sorbitan trioleate may be used.

Cationic surfactants preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The compositions of the invention may for example be formulated as wettable powders, dusts, granules, solutions, emulsifiable concentrates emulsions, suspension concentrates and aerosols. Wettable powders usually contain 25%, 50% or 75% w/w of active ingredient and usually contain in addition to solid inert carrier, 3%–10% w/w of a dispersing agent and, where necessary, 0%–10% w/w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5%–10% w/w of active ingredient. Granules are usually prepared to have a size between 10 and 100 mesh ASTM (approx. 2.00 mm–0.15 mm), and may be manufactured by agglomeration or impregnation techniques. Generally, granules will contain 0.5%–75% active ingredient and 0–10% w/w of additives such as stabiliser, surfactants, slow release modifiers and binding agents. The so called "dry flowable powders" consist of relatively small granules having a relatively high concentration of active ingredient. Emulsifiable concentrates usually contain, in addition to a solvent or a mixture of solvents, 1%–50% w/v active ingredient, 2%–20% w/v emulsifiers and 0%–20% w/v of other additives such as stabilisers, penetrants and corrosion inhibitors. Suspension concentrates are usually compounded so as to obtain a stable, nonsedimenting flowable product and usually contain 10%–75% w/w active ingredient, 0.5%–15% w/w of dispersing agents, 0.1%–10% w/w of suspending agents such as protective colloids and thixotropic agents, 0%–10% of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide slow release of the fungicidal compounds into the environment of a plant which is to be protected. Such slow-release formulations could, for example, be inserted in the soil adjacent to the roots of a plant, or could include an adhesive component enabling them to be applied directly to the stem of a plant.

As commodity the compositions may preferably be in a concentrated form whereas the end-user generally employs diluted compositions. The compositions may be diluted to a concentration of 0.001% of active ingredient (a.i.). The doses usually are in the range from 0.01 to 10 kg a.i./ha.

The compositions of this invention can comprise also other compounds having biological activity, e.g. compounds having similar or complementary fungicidal activity or compounds having plant growth regulating, herbicidal or insecticidal activity.

The other fungicidal compound can be, for example, one which is capable of combating diseases of cereals (e.g. wheat) such as those caused by Erysipha, Puccinia, Septoria, Gibberella and Helminthosporium spp., seed and soil borne diseases and downy and powdery mildews on vines and powdery mildew and scab on apples etc. These mixtures of fungicides can have a broader spectrum of activity than the compound of general formula I alone. Furthermore, the other fungicide can have a synergistic effect on the fungicidal activities of the compound of general formula 1.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclomezine, diethofencarb, difenoconazole, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoximmethyl, mancozeb, maneb, mepanipyrim, mepronil, metalaxyl, metconazole, methfuroxam, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, streptomycin, sulfur, tebuconazole, tecloftalame, tecnazene, tetraconazole, thiabendazole, thifluzamide, thiophanate-methyl, thiram, toiclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram In addition, the co-formulations according to the invention may contain at least one benzophenone of formula IA or IIA and any of the following classes of biological control agents such as viruses, bacteria, nematodes, fungi, and other microorganisms which are suitable to control insects, weeds or plant diseases or to induce host resisitance in the plants. Examples of such biological control agents are: *Bacillus thuringiensis, Verticillium lecanii, Autographica califomica* NPV, *Beauvaria bassiana, Ampelomyces quisqualis, Bacilis subtilis, Pseudomonas fluorescens, Steptomyces griseoviridis* and *Trichoderma harzianum.*

Moreover, the co-formulations according to the invention may contain at least one benzophenone of formula IA or IIA and a chemical agent that induces the systemic acquired resistance in plants such as for example nicotinic acid or derivatives thereof or BION.

The compounds of general formula I can be mixed with soil, peat or other rooting media for the protection of the plants against seed-borne, soil-borne or foliar fungal diseases.

The invention still further provides the use as a fungicide of a compound of the general formula IA or IIA as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLE 1

Preparation of 3-bromo-2,6,6'-trimethyl-2',3',4'-trimethoxybenzophenone 1A 3-Bromo-2,6-dimethylbenzonitrile A mixture of 2,6-dimethylbenzonitrile (5.0 g, 38.0 mmol), bromine (1.9 ml, 38.0 mmol) and chloroform (10 ml) is stirred at room temperature for 24 hours and subsequently heated to 60° C. for 6 hours. Upon cooling down to 0° C., 10 g of $AlCl_3$ are added and the mixture is stirred for 4 hours at 0° C. The reaction mixture is poured into water and extracted with toluene. The organic phase is separated and concentrated and the residue is purified by column chromatography yielding the pure product as brown crystals, 6.2 g, mp. 60° C.

1B 3-Bromo-2,6-dimethylbenzoic acid

A mixture of 1A (6.0 g) and sulfuric acid (18.0 g, 80%) is heated to 150° C. with stirring for 16 hours. The reaction mixture is diluted with ice-water and extracted with ethyl acetate. The organic phase is separated and concentrated and the residue is purified by column chromatography (petrol ether: ethyl acetate, 90:10 v/v) yielding the pure product as white crystals, 1.5 g, mp. 121° C.

1C 5-Bromo-2,6,6'-trimethyl-2',3',4'-trimethoxybenzophenone

A mixture of 1B (1.3 g, 5.7 mmol), 3,4,5-trimethoxytoluene (1.0 g; 5.7 mmol), $P_2O_5$ (3.5 g) and dichloromethane (20 ml) is stirred at room temperature for 16 hours. Subsequently, water (5 ml) and ice are added and dichloromethane is distilled off and the residue is extracted with toluene. The organic phase is washed with water and concentrated. The residue is recrystallized from petrol ethers/toluene. The solid material is collected by vacuum filtration, washed with cold petrol ethers and dried, yielding white crystals, 1.4 g, mp 859° C.

EXAMPLE 2

Preparation of 3-Bromo-2,6-dimethyl-2'-n-butoxy-3',4'-dimethoxybenzophenone

A mixture of n-butanol (5 ml) and sodium hydride (60% in oil, 20 mmol) is stirred until the formation of $H_2$ gas ceases. A mixture of 1C (2.0 g, 5.0 mmol) and dimethoxyethane (15 ml) is added to the resulting reaction mixture. Subsequently, the reaction mixture is heated to 90° C. with stirring for 14 hours and dimethoxyethane is distilled off. A mixture of water and ethyl acetate (1:1 v/v; 100 ml) is then slowly added at room temperature. The organic phase is separated, concentrated and the residue is purified by column chromatography (petrol ether: ethyl acetate, 90:10 v/v) yielding the pure product as a yellow oil, 1.7 g (78.3%).

EXAMPLES 3–49

Using essentially the same procedures described hereinabove for Examples 1 and 2 and employing standard derivatization techniques where appropriate, the following compounds are prepared and shown in Table I:

TABLE I

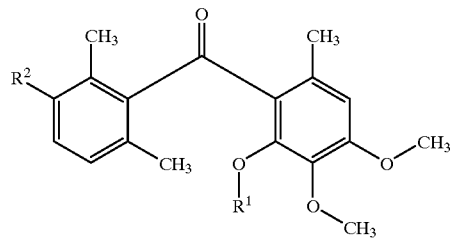

| Example | $R^1$ | $R^2$ | Melting point (°C.) |
|---|---|---|---|
| 3 | $CH_3$ | $NO_2$ | 138 |
| 4 | $CH_3$ | $CH_3O$ | 95 |
| 5 | $CH_3$ | Cl | oil |
| 6 | n-$C_5H_{11}$ | Br | oil |
| 7 | n-$C_3H_7$ | Br | oil |
| 8 | benzyl | Br | oil |
| 9 | $C_2H_5$ | Br | oil |
| 10 | pentafluorobenzyl | H | 132 |
| 11 | cyclohexylmethyl | H | 52 |
| 12 | benzyl | H | 76 |
| 13 | 2,4,6-trifluorobenzyl | H | 106 |
| 14 | 2,3,6-trifluorobenzyl | H | 87 |
| 15 | 2,4,5-trifluorobenzyl | H | 155 |
| 16 | 2,3,5-trifluorobenzyl | H | 86 |
| 17 | 3,5-difluorobenzyl | H | 83 |
| 18 | 3,4-difluorobenzyl | H | 96 |
| 19 | 2,5-difluorobenzyl | H | 142 |
| 20 | 2,3-difluorobenzyl | H | 79 |
| 21 | 2,4-difluorobenzyl | H | 83–84 |
| 22 | 2,6-difluorobenzyl | H | 110 |
| 23 | 3-fluorobenzyl | H | 65–69 |
| 24 | 2-fluorobenzyl | H | 90–91 |
| 25 | 4-fluorobenzyl | H | 93–94 |
| 26 | 2,6-dichlorobenzyl | H | 114–116 |
| 27 | 3,4-dichlorobenzyl | H | 105–106 |
| 28 | 2,4-dichlorobenzyl | H | 124–126 |
| 29 | 3-chlorobenzyl | H | 103–104 |
| 30 | 2-chlorobenzyl | H | 108–110 |
| 31 | 4-chlorobenzyl | H | 102–105 |
| 32 | 3-chloro-2-fluorobenzyl | H | 92 |
| 33 | 2-chloro-6-fluorobenzyl | H | 118–120 |
| 34 | 3-methylbenzyl | H | 74 |
| 35 | 3-methylbenzyl | H | 83–85 |
| 36 | 4-methylbenzyl | H | 104–105 |
| 37 | 3-methoxybenzyl | H | 92–64 |
| 38 | 4-methoxybenzyl | H | 99–101 |
| 39 | 4-tert-butylbenzyl | H | 88–90 |
| 40 | 2,4-dimethylbenzyl | H | 96–99 |

TABLE I-continued

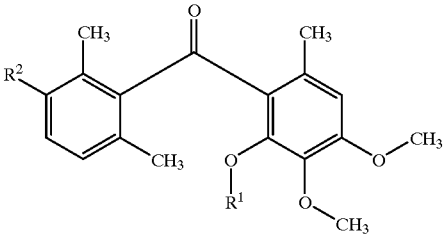

| Example | R¹ | R² | Melting point (°C.) |
|---------|-----|-----|---------------------|
| 41 | 2,5-dimethylbenzyl | H | oil |
| 42 | 4-trifluoromethylbenzyl | H | 112–113 |
| 43 | 3-trifluoromethylbenzyl | H | 119–121 |
| 44 | 4-bromobenzyl | H | 106–108 |
| 45 | 3-bromobenzyl | H | 122–123 |
| 46 | 2-bromobenzyl | H | 10/–108 |
| 47 | 3-methylbutyl | H | 81 |
| 48 | n-butyl | H | 75 |
| 49 | n-pentyl | H | oil |

Comparison experiment

Preparation of 3-Bromo-2,6-dimethyl-2'-n-butoxy-3',4'-dimethoxybenzophenone analogously to the method disclosed in EP 0727141

C-1 3-Bromo-2,6,6'-trimethyl-2'-hydroxy-3',4'-dimethoxy-benzophenone Aluminium chloride (1.25 g, 10 mmol) is added to a mixture of 5-bromo-2,6,6'-trimethyl-2',3',4'-trimethoxy-benzophenone obtained according to Example 1C (1.90 g, 4.7 mmol) and dichloromethane (5 ml). The mixture is stirred for 30 minutes at 0° C. and for 3 hours at ambient temperature. Subsequently the reaction mixture is poured into a mixture of ice and concentrated hydrochloric acid. The organic phase is separated and washed with dilute hydrochloric acid and water. The organic phase is dried and concentrated. The residue is purified by column chromatography (petrol ether: ethyl acetate, 95:5 v/v) yielding the pure product as yellow crystals, 1.2 g (67%).

C-2 3-Bromo-2,6-dimethyl-2'-n-butoxy-3',4'-dimethoxybenzophenone Potassium tert-butylat (0.55 g, 5 mmol) is added to a mixture of C-1 (1.90 g, 5 mmol) and dimethylformamide (4 ml). Upon stirring for 15 minutes at ambient temperature n-butylbromide (0.7 g, 5 mmol) is added to the reaction mixture. The mixture is stirred at ambient temperaure for 14 hours and subsequently poured into water. The aqueous phase is extracted with toluene. The combined organic phases are washed with dilute potassium hydroxide, and water. The organic phase is dried and concentrated. The residue is purified by column chromatography (toluene) yielding the pure product as a yellow oil, 1.3 g (73%). The overall yield starting from 1C in two steps was 49% compared with 78.3% obtained in one step with the process according to the invention (Example 2).

Biological Investigations

B Comparison of the curative and residual fungicidal activity of the substituted-2,6,6'-trimethylbenzophenones with a corresponding benzophenone unsubstituted in the 3-position Test diseases:

(a) Wheat Powdery Mildew (WPM):

HOST: Wheat (*Triticum aestivum* L.) variety Kanzler

PATHOGEN: *Erysiphe graminis* DC. f.sp. *tritici* E. Marchal (b) Cucumber Powdery Mildew (QPM):

HOST: Cucumber (*Cucumis sativus* L.) variety Bush pickle

PATHOGEN: *Erysiphe cichoracearum* DC

This test procedure is for curative and residual control of powdery mildew diseases.

1. Wheat seed (approximately 8–10/pot) or cucumber seed (1 seed/pot) is planted in 6 cm diameter plastic pots and maintained in the greenhouse.
2. When the primary leaf (wheat) or the cotyledons (cucumber) is/are fully expanded, formulated test compounds are sprayed with a single nozzle overhead track sprayer at a rate of 200 I/ha. Plants are then allowed to air-dry.
3. Inoculation precedes treatment by 2 days in the case of curative evaluations and follows treatment by 3 days in case of residual evaluations. For inoculation, plants are set up on greenhouse benches with bottom watering mats and inoculated by dusting them with conidia from powdery mildew infected plants (stock cultures at an age of 10–14 days). Between inoculation and treatment for curative evaluations and between treatment and inoculation for residual evaluations, plants are maintained in the greenhouse with bottom watering.
4. Disease on the primary leaf (wheat) or on the cotyledons (cucumber) as percent leaf area with disease symptoms/signs is evaluated about 7 days after inoculation. In the case of wheat, the tips and bases of the leaves are excluded from the evaluation.

Percent disease control is then calculated by the following formula:

$$\% \text{ disease control} = 100 - \frac{\% \text{ infection in treated plants}}{\% \text{ infection in untreated plants}} \times 100$$

Formulation, Reference Compounds And Controls:

1. Technical compounds are formulated in a solvent/surfactant system consisting of 5% acetone and 0.05% Tween 20 in deionized water. Compounds are dissolved in acetone prior to addition of the water; the Tween 20 can be added through either the acetone or the water. Dilutions are made using the solvent/surfactant system. Formulated compounds are prepared using deionized water.
2. Two kinds of controls are included: Plants treated with the solvent/surfactant solution and inoculated (Solvent Blank). Untreated plants which are inoculated (Inoculated Control).

The results of this evaluation are shown in Table II:

TABLE II

Curative and Residual Fungicidal activity of 2,6,6'-trimethylbenzophenones

| Example No. | a.i [ppm] | WPM 2 da Curative | WPM 3 da Residual | QPM 3 da Residual |
|---|---|---|---|---|
| 2 | 1250 | 92 | 100 | 100 |
|   | 125 | 90 | 100 | 89 |
|   | 12.5 | 87 | 100 | 0 |
| 3 | 1250 | 99 | 100 | 92 |
|   | 125 | 96 | 100 | 2 |
|   | 12.5 | 79 | 99 | 1 |
| 4 | 1250 | 94 | 100 | 98 |
|   | 125 | 86 | 100 | 13 |
|   | 12.5 | 73 | 100 | 0 |

TABLE II-continued

Curative and Residual Fungicidal activity of 2,6,6'-trimethylbenzophenones

| Example No. | a.i [ppm] | WPM 2 da Curative | WPM 3 da Residual | QPM 3 da Residual |
|---|---|---|---|---|
| 5 | 1250 | 96 | 100 | 100 |
|   | 125 | 93 | 100 | 66 |
|   | 12.5 | 83 | 100 | 11 |
| standard | 1250 | 92 | 100 | 89 |
|   | 125 | 74 | 81 | 6 |
|   | 12.5 | 55 | 70 | 14 |

In curative applications, application follows inoculation.
In residual applications, application precedes inoculation.

The following compound which is known from EP 0 727 141 has been used as standard:

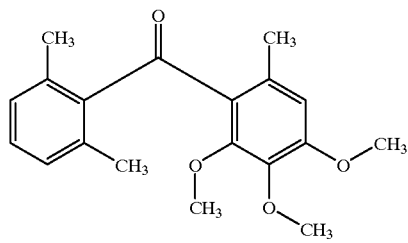

What is claimed is:

1. A compound of formula IA:

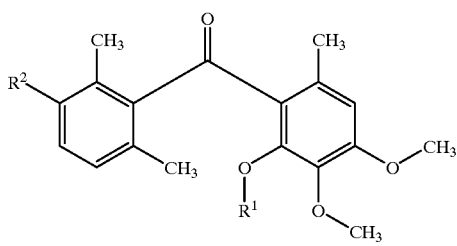

(IA)

wherein
  R¹ represents an optionally substituted $C_2-C_6$ alkyl, group, and
  R² represents a halogen atom, or an optionally substituted alkoxy group or a nitro group.

2. A compound as claimed in claim 1 being selected from the group consisting of
3-bromo-2'-butyloxy-3',4'-imethoxy-2,6,6'-trimethylbenzophenone,
2'-butyloxy-3-chloro-3',4'-dimethoxy-2,6,6'-trimethylbenzophenone,
2'-butyloxy-3',4'-dimethoxy-3-nitro-2,6,6'-trimethylbenzophenone,
2'-butyloxy-3,3',4'-trimethoxy-2,6,6'-trimethylbenzophenone.

3. A compound of formula IIA:

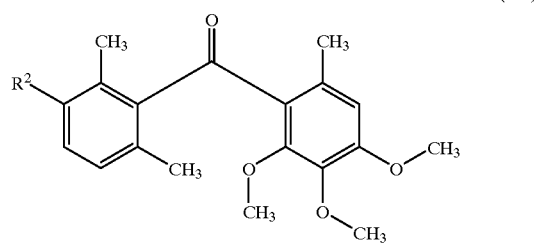

(IIA)

wherein
  R² represents a halogen atom, or an optionally substituted alkoxy group or a nitro group.

4. A compound as claimed in claim 3, wherein R² represents a chloro or bromo atom or a methoxy or a nitro group.

5. A compound as claimed in claim 4 being selected from the group consisting of
3-bromo-2',3',4'-trimethoxy-2,6,6'-trimethylbenzophenone,
3-chloro-2',3',4'-trimethoxy-2,6,6'-trimethylbenzophenone,
3-nitro-2',3',4'-trimethoxy-2,6,6'-trimethylbenzophenone, and
2',3,3',4'-tetramethoxy-2,6,69'-trimethylbenzophenone.

6. A composition which comprises a fungicidally effective amount of at least one compound of claim 1, and a carrier.

7. A composition which comprises a fungicidally effective amount of at least one compound of claim 3, and a carrier.

8. A method of combating fungus at a locus which comprises treating the locus with a compound of claim 1.

9. A method of combating fungus at a locus which comprises treating the locus with a compound of claim 3.

10. A method for combating fungus at a locus which comprises treating the locus with the composition as defined in claim 6.

11. A method of combating fungus at a locus which comprises treating the locus with the composition of claim 7.

12. The method according to claim 8 wherein the disease is caused by ascomycetes.

13. The method of claim 9 wherein the disease is caused by ascomycetes.

14. The method of claim 10 wherein the disease is caused by ascomycetes.

15. The method of claim 11 wherein the disease is caused by ascomycetes.

16. The method according to claim 10 wherein the fungus is a member of the taxonomic order Erysiphales.

17. The method according to claim 11 wherein the fungus is a member of the taxonomic order Erysiphales.

* * * * *